US012617842B2

(12) United States Patent
Schindler et al.

(10) Patent No.: US 12,617,842 B2
(45) Date of Patent: *May 5, 2026

(54) ANTIVIRAL IMMUNOTHERAPY BY MEMBRANE RECEPTOR LIGATION

(71) Applicant: Eberhard Karls Universitaet Tuebingen Medizinische Fakultaet, Tuebingen (DE)

(72) Inventors: Michael Schindler, Reutlingen (DE); Marius Codrea, Tuebingen (DE); Sven Nahnsen, Tuebingen (DE); Herwig Koppensteiner, Vienna (AT); Gundram Jung, Rottenburg-Wendelsheim (DE); Martin Hofmann, Tuebingen (DE)

(73) Assignee: Eberhard Karls Universitaet Tuebingen Medizinische Fakultaet, Tuebingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/541,134

(22) Filed: Dec. 2, 2021

(65) Prior Publication Data

US 2022/0153816 A1 May 19, 2022

Related U.S. Application Data

(63) Continuation of application No. 16/131,325, filed on Sep. 14, 2018, now Pat. No. 11,208,469, which is a continuation of application No. PCT/EP2017/056443, filed on Mar. 17, 2017.

(30) Foreign Application Priority Data

Mar. 18, 2016 (DE) .................... 10 2016 105 069.5

(51) Int. Cl.

| | |
|---|---|
| *C07K 16/10* | (2006.01) |
| *A61K 31/337* | (2006.01) |
| *A61K 35/17* | (2025.01) |
| *A61P 31/18* | (2006.01) |
| *C07K 16/28* | (2006.01) |
| *G01N 33/569* | (2006.01) |

(52) U.S. Cl.
CPC ........ *C07K 16/1045* (2013.01); *A61K 31/337* (2013.01); *A61K 35/17* (2013.01); *A61P 31/18* (2018.01); *C07K 16/2878* (2013.01); *G01N 33/56988* (2013.01); *C07K 2317/24* (2013.01); *C07K 2317/75* (2013.01)

(58) Field of Classification Search
CPC ........... C07K 16/2809; C07K 14/7051; C07K 16/2878; C07K 16/2827; C07K 2317/622; C07K 2317/32; C07K 2317/732; C07K 16/1045; C07K 2317/75; C07K 16/2896; C07K 16/2875; C07K 2317/24; C07K 2317/734; C07K 2317/55; C12N 5/0636; G01N 33/56988; A61P 31/18; A61P 35/00; A61K 51/00; A61K 35/17; A61K 2039/505

See application file for complete search history.

(56) References Cited

U.S. PATENT DOCUMENTS

| | | | |
|---|---|---|---|
| 7,812,133 | B2 | 10/2010 | Martin |
| 9,975,957 | B2 | 5/2018 | Du et al. |
| 10,017,572 | B2 | 7/2018 | Grogan et al. |
| 10,047,158 | B2 | 8/2018 | Grogan et al. |
| 2012/0141465 | A1 | 6/2012 | Croft et al. |
| 2013/0183315 | A1 | 7/2013 | Attinger et al. |
| 2014/0377284 | A1 | 12/2014 | Simons et al. |
| 2015/0190506 | A1 | 7/2015 | Cheung et al. |

FOREIGN PATENT DOCUMENTS

| | | |
|---|---|---|
| DE | 60317677 T2 | 10/2008 |
| EP | 1997893 A1 | 12/2008 |
| EP | 2650020 A1 | 10/2013 |
| RU | 2426744 C2 | 11/2007 |
| WO | 99/42585 A1 | 8/1999 |
| WO | 2013/038191 A2 | 3/2013 |

OTHER PUBLICATIONS

Liu et al. AIDS Vaccine 2009, p. 1.*
Weiberg et al. J. Immunotherapy, 2006, vol. 29, No. 6, pp. 575-585.*
Kunar et al. Mediator Inflammation. 2013, pp. 2-13.*
Takahashi et al. J Virol. Aug. 2001; 75(15): 6748-6757.*
Tanaka et al. AIDS Research and Human Retroviruses, published by 2010, vol. 26, No. 10, pp. 1147-1154.*
Kondo et al. Human Immunology, vol. 68, Issue 7, Jul. 2007, pp. 563-571.*
Examination Report for Japanese Application No. 2020-16152, dated Jul. 19, 2022 (1 page).
A.E. Sousa, et al. "Early Reduction of the Over-Expression of CD40L, OX40 and Fas on T Cells in HIV-1 Infection During Triple Anti-Retroviral Therapy: Possible Implications for Lymphocyte Traffic and Functional Recovery." Clin. Exp. Immunol., 116: 307-315 (1999) (9 pages).
First Office Action for Chinese Patent Application CN201780017932. 9, dated Apr. 1, 2021, 10 pages with extra 14 pages of English language equivalent or summary.
Nyakeriga, et al. "Highly Active Antiretroviral Therapy in Patients Infected with Human Immunodeficiency Virus Increases CD40 Ligand Expression and IL-12 Production in Cells Ex Vivo." Viral Immunology, vol. 24, No. 4, 2011, pp. 281-289. doi.org/10.1089/vim.2010.0142.

(Continued)

*Primary Examiner* — Bao Q Li

(57) ABSTRACT

The present invention relates to a cytotoxic agent for the prophylaxis and/or treatment of a viral infection which is configured for the selective binding to a membrane receptor of virus-infected T lymphocytes, a pharmaceutical composition containing said cytotoxic agent, the use of the cytotoxic agent for the prophylaxis and/or treatment of viral infections, a method of finding cytotoxic agents, the use of a membrane receptor of virus-infected T lymphocytes which is overexpressed in comparison to non-infected T lymphocytes for the diagnosis of a viral infection.

8 Claims, 2 Drawing Sheets

(56) References Cited

OTHER PUBLICATIONS

Tanaka, et al. "Suppression of CCR5-Tropic HIV Type 1 Infection by OX40 Stimulation via Enhanced Production of β-Chemokines." AIDS Research and Human Retroviruses, vol. 26, No. 10, 2010, pp. 1147-1154. doi.org/10.1089/aid.2010.0043.

Tsuruno, et al. "A Recombinant Vesicular Stomatitis Virus Encoding HIV-1 Receptors and Human OX40 Ligand Efficiently Eliminates HIV-1-Infected CD4-Positive T Cells Expressing OX40." Human Immunology, vol. 72, Issue 4, Apr. 2011, pp. 295-304. doi.org/10.1016/j.humimm.2011.01.007.

Decision of Refusal for Japanese Patent Application JP2018-549270, dated Jul. 21, 2020, 5 pages.

Further Examination Report for New Zealand Patent Application NZ746316, dated Jun. 3, 2020, 9 pages.

Palanee, et al. "Study on the Expression of Co-Stimulatory Marker CD134 on CD4+ T Cells in HIV-1-Infected Individuals." Journal of Immunoassay and Immunochemistry, 2012, vol. 33, pp. 195-202. DOI: 10.1080/15321819.2011.618861.

Notification of Reasons for Refusal for Japanese Patent Application JP2018-549270, dated Oct. 15, 2019, 7 pages with extra 11 pages of English language equivalent or summary.

Sousa, et al. Exp. Immunol., May 1999, vol. 116, No. 2, pp. 307-315.

Examination Report for New Zealand Patent Application NZ746316, dated Jul. 19, 2019, 10 pages.

Seddiki, N., et al. "Human Antigen-Specific CD4+CD25+CD134+ CD39+ T Cells are Enriched for Regulatory T Cells and Comprise a Substantial Proportion of Recall Responses." European Journal of Immunology, Apr. 29, 2014, 44(6): 1644-1661. doi.org/10.1002/eji.201344102.

International Preliminary Report on Patentability for Patent Application PCT/EP2017/056443, dated Sep. 18, 2018, 11 pages.

Notification of Transmittal of Translation of the International Preliminary Report on Patentability for Patent Application PCT/EP2017/056443, dated Sep. 27, 2018, 1 page.

Examination Report for Russian Patent Application RU2018/1340,22/04(055948), dated Jun. 25, 2019, 8 pages.

Examination Report for Russian Patent Application RU2018/1340,22/04(055948), dated Jun. 25, 2019, 7 pages (an English language of an equivalent or summary).

Kumar, et al. "TNF and TNF Receptor Superfamily Members in HIV Infection: New Cellular Targets for Therapy?" Hindawi Publishing Corporation, Mediators of Inflammation, vol. 2013, Article ID 484378, dated Nov. 24, 2013, 13 pages. http://dx.doi.org/10.1155/2013/484378.

Curti, et al. "OX40 is a Potent Immune Stimulating Target in Late Stage Cancer Patients." NIH Public Access, Cancer Res., dated Dec. 15, 2013, 73(24), pp. 7189-7198. doi:10.1158/0008-5472.CAN-12-4174.

Weinberg, et al. "Anti-OX40 (CD134) Administration to Nonhuman Primates: Immunostimulatory Effects and Toxicokinetic Study." J. Immunother. vol. 29, No. 6, Nov./Dec. 2006, pp. 575-585.

Bulliard, et al. "OX40 Engagement Depletes Intratumoral Tregs via Activating FcγRs, Leading to Antitumor Efficacy." Immunology and Cell Biology (2014) 92, dated Apr. 15, 2014, pp. 475-480.

Kibbe, A. Handbook of Pharmaceutical Excipients, 4th Edition, American Pharmaceutical Association . . . => Only cited in respect of pharmaceutical acceptable carrier but not relevant for assessing patentability. It is therefore reframed from providing a copy of this textbook.

International Search Report and Written Opinion for Application No. PCT/EP2017/056443, dated Mar. 17, 2017.

Ammaranoud, et al. (2012) "Study on the Expression of Co-Stimulatory Marker CD134 on CD4+ T Cells in HIV-1-Infected Individuals." Journal of Immunoassay and Immunochemistry, 33:2, pp. 195-202.

Wei Jiang, et al. (2014) Cycling Memory CD4+ T Cells in HIV Disease have a Diverse T Cell Receptor Repertoire and a Phenotype Consistent with Bystander Activation. Journal of Virology, vol. 88, No. 10, pp. 5369-5380.

Andrew D. Weinberg, et al. (2011) "Science Gone Translational: the OX40 Agonist Story." Immunological Reviews, 2011, vol. 244, pp. 218-231.

PCT/EP2017/056443, Filing Receipt dated Mar. 17, 2017.

Office Action for European Patent Application 17711660.5, dated Jan. 28, 2022, 7 pages.

Kuo Hsiao-Hsuan, et al. "Anti-Apoptotic Protein BIRC5 Maintains Survival of HIV-1-Infected CD4+ T Cells." Immunity, Bd. 48, Nr. 6, Jun. 19, 2018, Seiten 1183-1194.e5.

Office Action for Chinese Patent Application 201780017932.9, dated Jan. 30, 2022 (28 pages).

Correction of Notice of Allowability for U.S. Appl. No. 16/131,325, dated Sep. 22, 2021 (2 pages).

Correction of Notice of Allowability for U.S. Appl. No. 16/131,325, dated Sep. 15, 2021 (4 pages).

Notice of Allowance for U.S. Appl. No. 16/131,325, dated Aug. 20, 2021 (8 pages).

Examiner-Initiated Interview Summary for U.S. Appl. No. 16/131,325, dated Aug. 12, 2021 (1 page).

Response to Non-Final Office Action for U.S. Appl. No. 16/131,325, dated Jun. 24, 2021 (10 pages).

Non-Final Office Action for U.S. Appl. No. 16/131,325, dated Jan. 26, 2021 (7 pages).

Response to Final Office Action for U.S. Appl. No. 16/131,325, dated Nov. 4, 2020 (9 pages).

Final Office Action for U.S. Appl. No. 16/131,325, dated Jun. 4, 2020 (9 pages).

Response to Non-Final Office Action and Declaration of Michael Schindler for U.S. Appl. No. 16/131,325, dated Apr. 29, 2020 (39 pages).

Non-Final Office Action for U.S. Appl. No. 16/131,325, dated Oct. 31, 2019 (12 pages).

Response to Restriction Requirement for U.S. Appl. No. 16/131,325, dated Oct. 18, 2019 (7 pages).

Restriction Requirement for U.S. Appl. No. 16/131,325, dated Aug. 19, 2019 (8 pages).

Andred D. Weinberg, et al.; "Science Gone Translational: the Ox40 Agonist Story"; Immunological Reviews (2011) pp. 218-231; vol. 244.

Brendan D. Curti, et al.; "OX40 is a Potent Immune-Stimulating Target in Late-Stage Cancer Patients"; Microenvironment and Immunology; Cancer Research (2013) pp. 7189-7198; doi: 10.1158/0008-5472.CAN-12-4174.

Chikayuki Tsuruno, et al.; "A recombinant vesicular stomatitis virus encoding HIV-1 receptors and human OX40 ligand efficiently eliminates HIV-1-infected CD4-positive T cells expressing OX40"; Human Immunology; American Society for Histocompatibility & Immunogenetics; (2011) pp. 295-304; vol. 72.

Amit Kumar, et al.; "TNF and TNF Receptor Superfamily Members in HIV infection: New Cellular Targets for Therapy?"; Hindawi Publishing Corporation; Mediators of Inflammation (2013) pp. 1-13; vol. 2013; Article ID 484378; http://dx.doi.org/10.1155/2013/484378.

Qigui Yu, et al.; "OX40 Ligation of CD4+ T Cells Enhances Virus-Specilc CD8+ T Cell Memory Responses Independently of IL-2 and CD4+ T Regulatory Cell Inhibition"; The Journal of Immunology; Feb. 15, 2006; pp. 2486-2495; vol. 176 (4); https://doi.org/10.4049/jimmunol.176.4.2486.

Ronald Mitsuyasu; "Curing HIV: lessons from cancer therapy," Curr Opin HIV AIDS. May 2013 ; 8(3): 224-229. doi:10.1097/COH.0b013e32835ef0a1.

* cited by examiner

ANTIVIRAL IMMUNOTHERAPY BY MEMBRANE RECEPTOR LIGATION

CROSS REFERENCES TO RELATED APPLICATIONS

This application is a continuation application of U.S. patent application Ser. No. 16/131,325, filed on Sep. 14, 2018, entitled "ANTIVIRAL IMMUNOTHERAPY BY MEMBRANE RECEPTOR LIGATION", now allowed, which is a continuation of copending international patent application PCT/EP2017/056443 filed on 17 Mar. 2017 and designating the U.S., which has been published in German, and claims priority from German patent application DE 10 2016 105 069.5 filed on 18 Mar. 2016. The entire contents of these prior applications are incorporated herein by reference in their entireties for all purposes.

FIELD

The present invention relates to a cytotoxic agent for the prophylaxis and/or treatment of a viral infection, which is configured for the selective binding to a membrane receptor of virus-infected T lymphocytes, a pharmaceutical composition containing said cytotoxic agent, the use of the cytotoxic agent for the prophylaxis and/or treatment of viral infections, a method of finding cytotoxic agents, the use of a membrane receptor of virus-infected T lymphocytes, which is overexpressed in comparison to non-infected T lymphocytes, for the diagnosis of a viral infection.

BACKGROUND

Viral infections are one of the great challenges of the present to science and medicine. One of the human patho-genic viruses in focus is the human immunodeficiency virus (HIV). HIV is an enveloped virus belonging to the family of the retroviruses and to the genus of the lentiviruses. An untreated HIV infection usually leads to AIDS (acquired immunodeficiency syndrome) after a latency phase of vary-ing lengths free of symptoms, usually lasting several years. The worldwide HIV prevalence in adults at the age of 15 to 49 years was 0.8 percent in the year 2010. For Central and Western Europe, it was 0.2 percent. It was above average in Subsaharian Africa (5.0 percent) and the Caribbean (0.9 percent). In some states, such as Swaziland, Botswana or Lesotho, about one quarter of the 15 to 49 years old are infected with the HI virus. In Germany, the HIV prevalence in the year 2009 was approximately 0.1 percent.

For the proliferation, the HI virus requires host cells carrying the so-called CD4 receptor on the surface. These are mainly CD4 bearing T helper cells, so-called CD4$^+$ cells or CD4$^+$ lymphocytes. The main reservoir for the HI viruses is the follicular T helper cells in the body's lymphoid follicles, which make up about 2% of the CD4$^+$ cells. Latent infected, resting CD4$^+$ T cells or T memory cells, respec-tively, represent long lasting reservoirs for HIV. These cells are held responsible for the fact that despite the currently available antiretroviral drugs HIV cannot be eradicated yet and that recurrences occur repeatedly after discontinuation of the therapy.

Since the proliferation of the viruses takes place inside of normal cells and is closely linked to the central biochemical cell mechanisms, the antiviral agents in question must either prevent the penetration of the virions into the host cells, intervene in the cell metabolism to the detriment of the virus proliferation or, after a possible virus proliferation in the cells, prevent the new viruses from escaping from the cells.

On the other hand, however, these sought-after active agents must also be tolerable to the body's metabolism, the cell structure and/or the internal cell metabolism as a whole, as otherwise not only the virus proliferation in the cells but in the worst case also the (cellular) life of the entire treated organism comes to a standstill.

Because these conditions are very difficult to reconcile, some of the antiviral drugs developed so far are often associated with serious side effect risks.

The current therapy of choice for an HIV infection and AIDS is called highly active antiretroviral therapy (HAART). HAART is a combined drug therapy consisting of at least three antiretroviral agents. Several classes of active ingredients are currently used: Nucleoside and nucleotide analogues (NRTI), non-nucleoside reverse tran-scriptase inhibitors (NNRTI), HIV protease inhibitors (PI), entry and fusion inhibitors and integrase inhibitors.

Some of the afore-mentioned active agents are referred to as 'direct acting antiviral drugs' (DAA). DAA specifically inhibit viral proteins, but not cellular proteins of the host. This principle of action should lead to fewer side effects.

However, it is precisely in DAA that the viruses to be attacked also develop resistance, which they are well able to do so because of their extremely fast reproduction cycle and the biochemical characteristics of this replication.

Furthermore, a disadvantage of the currently used antivi-ral agents is that they are virostatic, but not virotoxic. They inhibit the proliferation of the viruses, but do not kill them.

SUMMARY

Against this background, it is an object of the present invention to provide a novel antiviral agent with which the disadvantages of the currently available antiviral agents are reduced, possibly even avoided. As far as possible, such an active agent should be provided which kills the virus or the virus-infected cell, i.e. which is virotoxic.

This object is achieved by the provision of a cytotoxic agent, which is configured for the selective binding to a membrane receptor of virus-infected T lymphocytes, wherein the membrane receptor is selected from the group consisting of: CD134, CD132, CD71, CD70, CD54, CD39, BTLA, CD97, CD2, CD63, CD50, CD161, CD218, CD226, CD7, CD49d, and CD29.

Using a novel FACS-based screening method, the inven-tors could surprisingly find that the afore-mentioned mem-brane receptors are significantly overexpressed in virus-infected T lymphocytes compared to non-virus-infected T lymphocytes. Thus, these membrane receptors at first enable the identification of virus-infected T lymphocytes.

An association between the afore-mentioned membrane receptors and the viral infection of T lymphocytes has not yet been described in the state of the art. They therefore represent a new biomarker with therapeutic implications.

The cytotoxic agent according to the invention makes use of the phenomenon recognized by the inventor. It selectively binds to virus-infected T lymphocytes and displays its cytotoxic activity there. Non-infected cells are not or sig-nificantly weaker bound. Side effects are thus minimized.

In contrast to most of the currently available therapeutics against viral diseases, the cytotoxic agent according to the invention does not only have a virostatic effect, thus not only prevents the spread and proliferation of the viruses. The cytotoxic agent according to the invention rather has a virotoxic effect and thus has the potential to selectively eliminate the infected T lymphocytes and the viruses and precursors of the viruses present in the cells.

The cytotoxic agent according to the invention thus satisfies a long standing need for causally effective therapeutics in the treatment of infectious viral diseases.

An "agent" is understood according to the invention to mean a substance which, on account of its chemical-physical properties, acts on the viability and/or proliferation of the virus-infected T lymphocyte. The agent may be a chemically defined compound, an active ingredient, a medicament etc.

According to the invention, "cytotoxic" means such an activity which exerts an inhibiting influence on the viability and/or proliferation of the virus-infected T lymphocytes.

A "selective binding" is understood according to the invention to be a targeted and specific coupling of the cytotoxic agent to the membrane receptor, which is based on a selective interaction according to the key-lock-principle. It is distinct from a non-selective binding, which is based on non-specific interactions between the agent and the receptor.

"T lymphocytes" form a group of white blood cells which serve the immune response and, according to the invention, comprise all T cells, in particular T helper or memory cells, which carry the CD4 receptor (CD4+ T lymphocytes).

"CD" stands for 'cluster of differentiation' and refers to groups of immunophenotypic surface characteristics of cells that can be classified according biochemical or functional criteria. The CD molecules are mostly membrane bound glycoproteins, which are often cell-specifically expressed and may have a variety of functions: Some CDs have receptor or signaling function, while others have been shown to have encymatic activity; in addition, some cluster molecules are attributed a central role in the intercellular communication.

"CD134", also known as tumor necrosis factor receptor superfamily member 4 (TNFRSF4) or OX40, is a member of the TNFR superfamily of the receptors that is constitutively expressed on resting naive T-cells. CD134 is a secondary, co-stimulating immune checkpoint molecule. It is assumed that CD134 has no effect on the proliferating activity of CD4+ T cells during the first three days, but after this time the proliferation slows down and the cells die to an increased extend. CD134 has been described to be involved in the pathological so-called cytokine storm associated with various viral infections, such as H5N1 avian influenza, an overreaction of the immune system that produces high concentrations of inflammatory cytokines which in turn cause the leucocytes to form additional cytokines.

"CD132", also referred to as common gamma chain (γc) or interleukin 2 receptor subunit gamma (IL-2RG), is a cytokine receptor subunit common to the receptor complexes of at least six different interleukin receptors: IL 2, IL 4, IL 7, IL 9, IL 15 and IL 21 receptors. Lymphocytes expressing CD132 can form functional receptors for these cytokines. The prior art has described diseases associated with dysfunctions or mutations in CD132, such as X-SCID ('severe combined immunodeficiency') or schizophrenia.

"CD71", also known as "transferrin receptor protein 1" (TfR1), is a transmembrane protein, necessary for the transport of transferrin into the cells by endocytosis. CD71 is described as a potential target structure in cases of human leukemia and lymphoma.

"CD70" is a protein that is activated on highly activated lymphocytes, such as in T and B cell lymphomas. It is therefore assumed that anti CD70 antibodies represent a possible form of therapy for CD70 positive lymphomas.

"CD54", also known as ICAM 1 (intracellular adhesion molecule 1), is a transmembrane glycoprotein which is typically expressed on endothelial cells and cells of the immune system. It is a member of the immunoglobulin superfamily. After cytokine stimulation there is a strong increase in the CD54 concentration. CD54 is indicated by interleukin 1 (IL 1) and tumor necrosis factor (TNF) and is expressed by the vascular endothelium, macrophages and lymphocytes. CD54 play inter alia an important role in the signal transduction of the cells. CD54 is associated with subarachnoid hemorrhage (SAH), in which free blood enters the subarachnoid space filled with cerebrospinal fluid.

"CD39", also known as "ectonucleoside triphosphate diphosphohydrolase-1" (ENTPD1), is a transmembrane protein which catalyzes the hydrolysis of γ- and β-phosphate residues of triphospho- and diphosphonucleosides to monophosphonucleoside derivates.

"BTLA", also referred to as "CD272" is induced during the activation of T cells. It causes a T cell inhibition through the interaction with receptors of the tumor necrosis factor. An activation of BTLA is implicated in the inhibition of the function of human CD8+ cancer specific T cells.

"CD97" or "BL-Ac[F2]" is a member of the adhesion GPCR family. CD97 is expressed on hematopoetic stem or progenitor cells, immune cells, epithelial cells, muscle cells and their malignant variants. In the immune system, CD97 plays the role of a critical mediator of the host defense. Outside of the immune system, CD97 may be involved in cell-cell interactions. CD97 is found in a variety of tumors, including those of the thyroid, stomach, pancreas, esophagus, colon, and oral squamous cell carcinomas.

"CD2" is a cell adhesion molecule found on the surface of T cells and natural killer cells (NK cells). Other designations include T cell surface antigen T11/Leu-5, LFA 2, LFA 3 receptor, erythrocyte receptor and rosette receptor. CD2 interacts with other adhesion molecules. A large proportion of T cell lymphomas and leukemias express CD2, so that in the state of the art CD2 is used to discriminate these states from B cell neoplasms.

"CD50" or "intracellular adhesion molecule 3" (ICAM 3) is a transmembrane glycoprotein. It is expressed constitutively and strongly by all leucocytes and is considered one of the most important ligands for LFA 1 in the initiation of the immune response.

"CD161", also referred to as "killer cell lectine-like receptor subfamily B member 1", "NK1.1", "KLRB1", "NKR P1A", is a transmembrane glycoprotein which is expressed by NK cells and appears to be involved in the regulation of the NK cell function.

"CD218" or "Interleukin 18 receptor alpha" (IL 18 Ra) is a member of the IL 1 receptor superfamily. CD218 is expressed on Th1 cells, a subtype of NK cells, neutrophiles and IL 12 stimulated tonsile B cells. CD218 seems to play an important role in the innate immune response and autoimmune reactions.

"CD226", also known as "PTA1" ("platelet and T cell activation antigene 1") or "DNAM 1" ("DNAX accessory molecule 1"), is a transmembrane glycoprotein expressed on the surface of NK cells, platelets, monocytes and a fraction of T cells. CD226 mediates the cellular adhesion to other cells carrying their ligands, CD112 and CD155.

"CD7" is a transmembrane protein which is expressed on thymocytes and mature T cells. It plays an important role in T cell interactions during the early development of the lymphatic system.

"CD49d" is an integrin alpha subunit that forms a part of the α4β1 lymphocyte homing receptor. It interacts with LGALS8 and paxillin.

"CD29" or "integrin beta 1" is an integrin subunit, which for example, interacts with the alpha 3 subunit to form the α3β1 -complex, which reacts with molecules such as netrin 1 and reelin. As with other integrines, CD129 is involved in cell adhesion and cell recognition in a variety of processes, including the embryonic development, hemostasis, tissue repair, immune response and metastatic spread of tumor cells.

The over expression of the afore-mentioned membrane receptors in virus-infected T lymphocytes, e.g. in HIV-infected CD4+ T lymphocytes, was surprising and not suggested by the state of the art. It was therefore not to be expected.

The object underlying the invention is hereby completely achieved.

According to an embodiment of the invention, the cyto-toxic agent is coupled to a binding molecule which is selective for the membrane receptor.

With this measure the invention takes advantage of the properties of compounds to bind to the membrane receptors found by the inventor in a highly specific and selective way. A "binding molecule" includes any compound capable of selectively and specifically coupling or ligating the cytotoxic agent to at least one of the membrane receptors CD134, CD132, CD71, CD70, CD54, CD39, BTLA, CD97, CD2, CD63, CD50, CD161, CD218, CD226, CD7, CD49d, and CD29.

According to a further embodiment of the invention, the binding molecule is selected from the group consisting of: immunoglobulin, immunoglobulin fragment, aptamer, low molecular weight compound, receptor, receptor fragment, cytokine.

With this further development of the invention, such binding molecules are used which are particularly well-suited for the selective and specific coupling of the cytotoxic agent to the identified overexpressed membrane receptors.

The immunoglobulin may be an immunoglobulin, and antibody, preferably an agonistic antibody.

According to the findings of the inventor, the cytotoxic agent can be coupled particularly advantageously to such a binding molecule and can be bound specifically and selectively to one of the identified membrane receptors of virus-infected T lymphocytes.

In an embodiment of the invention, the immunoglobulin is selected from the group consisting of: MEDI6469 (9612), MEDI6383, MEDI0562, Hu106-222/Hu119-122 (UTM-DACC).

These are antibodies which are preferred according to the invention and are directed against the CD134 membrane receptor, and they are therefore particularly suitable as a binding molecule. MEDI6469 is an agonistic murine antibody from MedImmun, AstraZeneca, which is currently being tested for the treatment of solid tumors in humans in a phase I clinical trial.

The suitability of the antibodies mentioned above for the purpose of the cytotoxic treatment of a viral infection was surprising. Anti-CD134 antibodies are described in the state of the art, such as for example in Weinberg et al. (2006), Anti-OX40 (CD134) Administration to Nonhuman Primates: Immunostimulatory Effects and Toxokinetic Study, J. Immunother., Vol. 29, Nr. 6, S. 575-585, however as a component or in combination with a vaccine or as an immunostimulating agent. Unlike the invention, there the anti-CD134 antibody does not aim to have toxic effects on virus-infected cells but rather to have immunostimulating effects on the entire organism.

The immunostimulating effect of anti-CD134 antibodies is also disclosed, primarily in connection with the treatment of cancers, in WO 99/42585, EP 1 997 893, EP 650 020, WO 2013/038191, Curti et al. (2013), OX40 is a Potent Immune-Stimulating Target in Late-Stage Cancer Patient, Cancer Res. 73(24), S. 7189-7198; Bulliard et al. (2014), OX40 Engagement Depletes Intratumoral Tregs via activating FcγRs, Leading to Antitumor Efficacy, Immunology and Cell Biology 92, S. 475-480.

According to a further embodiment of the cytotoxic agent according to the invention, the virus-infected T lymphocytes are virus-infected CD4+ T lymphocytes.

This measure has the advantage that the cytotoxic agent according to the invention specifically and selectively eliminates T lymphocytes that serve as long lasting reservoirs of viruses in the case of an HIV infection. The elimination of these cells by the cytotoxic agent according to the invention not only results in a drastic reduction of the viral load, it also prevents recurrences during or after the discontinuation of therapy.

Against this background, a preferred viral infection to be treated or prevented according to the invention is an HIV infection.

According to a further embodiment of the invention, the cytotoxic agent comprises a cytostatic agent.

This measure has the advantage that for a targeted elimination of virus-infected T lymphocytes such an active ingredient is used, which has been proven in other indications, such as, for example, a cancer disease. As a result, empirical values relating to dosage, formulation, side effect spectra, etc. can be used.

In a further embodiment, the cytostatic agent is selected from the group consisting of: alkylating agents, platinum analogues, intercalants, antibiotics, mitosis inhibitors, taxanes.

With the mentioned cytostatics such drugs are used which are extensively researched and available with adequate drug safety. They are therefore particularly suitable for achieving the purpose of the invention.

According to an embodiment, the cytotoxic agent according to the invention comprises a virostatic agent.

This measure has the advantage that the virotoxic inherent effect if the agent according to the invention is supplemented by a virostatic effect. The therapeutic effectiveness of the cytotoxic agent according to the invention is thus further increased.

Against this background, another subject-matter of the invention is a pharmaceutical composition comprising the cytotoxic agent according to the invention and a pharmaceutically acceptable carrier.

Pharmaceutically acceptable carriers are well-known in the art. For example, reference is made to the treatise by Kibbe A. (2003), Handbook of Pharmaceutical Excipients, 4th Edition, American Pharmaceutical Association and Pharmaceutical Press.

The embodiments, further developments, features, properties and advantages of the cytotoxic agent according to the invention apply equally to the pharmaceutical composition according to the invention.

Another subject matter of the invention is the use of a cytotoxic agent for the prophylaxis and/or treatment of a viral infection, which is configured for a selective binding to a membrane receptor of virus-infected T lymphocytes, wherein the membrane receptor is selected from the group consisting of: CD134, CD132, CD71, CD70, CD54, CD39, BTLA, CD97, CD2, CD63, CD50, CD161, CD218, CD226, CD7, CD49d, and CD29.

The embodiments, further developments, features, properties and advantages of the cytotoxic agent according to the invention apply equally to the use according to the invention.

Another subject matter of the invention is a method for the finding of cytotoxic agents, which comprises the selection of such compounds which can selectively bind to a membrane receptor of virus infected T lymphocytes, wherein the membrane receptor is selected from the group consisting of: CD134, CD132, CD71, CD70, CD54, CD39, BTLA, CD97, CD2, CD63, CD50, CD161, CD218, CD226, CD7, CD49d, and CD29.

The inventors thus provide a method that not only makes available cytotoxic agents already known in the state of the art, such as MEDI6469 (9B12), but also new compounds not previously known or characterized. Substance libraries can be screened for this purpose. The substances are brought into contact with the membrane receptors under suitable experimental conditions. It is determined whether a specific and selective binding occurs between the substances and the membrane receptors. Specifically and selectively binding substances are potential cytotoxic agents according to the invention.

The embodiments, further developments, features, properties and advantages of the cytotoxic agent according to the invention apply equally to the method according to the invention.

Another subject matter relates to a method for the diagnosis of a viral infection, comprising determining any overexpression of a membrane receptor of virus-infected T lymphocytes over uninfected T lymphocytes, wherein the membrane receptor is selected from the group consisting of: CD134, CD132, CD71, CD70, CD54, CD39, BTLA, CD97, CD2, CD63, CD50, CD161, CD218, CD226, CD7, CD49d and CD29.

The inventors have realized that the overexpressed mentioned membrane receptors are diagnostic markers via which a viral infection can be reliably detected. The detection of an overexpression on T lymphocytes correlates with the prevalence of a virus expression.

The embodiments, further developments, features, properties and advantages of the cytotoxic agent according to the invention apply equally to the method according to the invention.

Yet another subject matter of the invention is a method for the determination of surface structures on virus-infected T lymphocytes, preferably membrane receptors, which are suitable as a target of cytostatic agents, wherein the method comprises the infection of T lymphocytes with a virus and the determination of any overexpression of the surface structures on the virus-infected T lymphocytes over non-effected T lymphocytes.

The inventors have developed a model in which initially T lymphocytes are infected by viruses, for example HI viruses. The next step is to analyze which surface structures which are suitable as targets for a cytotoxic agent, are overexpressed on the infected T lymphocytes. The stronger the overexpression in comparison to non-infected T lymphocytes, the more selective and the better suited as the cytotoxic agent according to the invention is a substance which binds highly specifically to this surface structure.

It is understood that the features mentioned above and those yet to be explained in the following can be used not only in the particular combination indicated, but also in other combinations or in isolated position, without departing from the scope the present invention.

The present invention will now be explained in more detail by means of exemplary embodiments from which further features, properties and advantages of the invention result. The embodiments are not limiting.

It is understood that individual features disclosed in the embodiments are disclosed not only in the context of the very specific embodiment but in a general sense and in themselves provide a separate contribution to the invention. The person skilled in the art can therefore freely combine these features with other features of the invention.

EXAMPLES

1. Screening of HIV-1 Infected T Lymphocytes

Figures 1A, 1B:
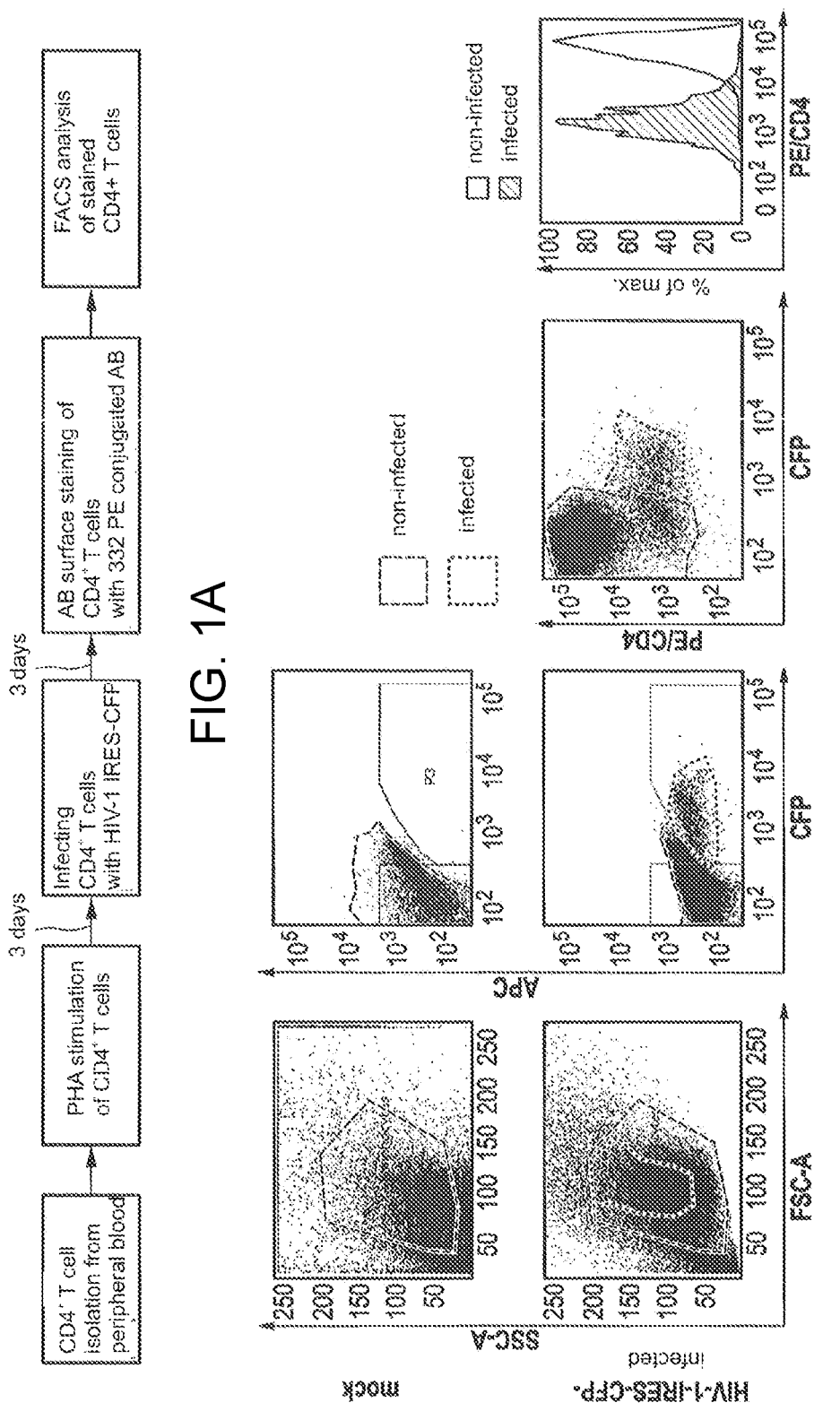
FIG. 1A shows schematically the establishment of a screening method for the determination of surface structures in HIV-1 infected T lymphocytes, which is the basis for the finding of the cytotoxic agents according to the invention.
FIG. 1B shows FACS analysis of stained CD4+ T cells.

CD4+ T lymphocytes were isolated from the peripheral blood of healthy donors. The isolated CD4+ T lymphocytes were stimulated with phytohaemagglutinin (PHA) for three days. Subsequently, the cells so stimulated were infected with HIV-1 expressing CFP ('cyan fluorescent protein') via an internal ribosomal entry site (IRES) together with the nef open reading frame. The surface of the infected CD4+ T lymphocytes was stained for 48 to 72 hours after the infection with 332 PE conjugated antibodies presented in four 96 well micro titer plates. To switch off the autofluorescence, infected and non-infected cells were filtered against allophycocyanin (APC). For the analysis, the PE average values of infected CFP-positive cells and non-infected CFP-negative cells were used. The establishment of the receptor surface screening in HIV-1 infected CD4+ T lymphocytes is shown schematically in FIGS. 1A and 1B.

2. Overexpression of Membrane Receptors in HIV-1 Infected T Lymphocytes 48 up to 72 hours after the infection of CD4+ T lymphocytes, the overexpression of membrane receptors that have already been described in the state of the art in connection with an HIV-infection, such as CD45RO, CD25, CD150 and CD279 is shown as expected. These results confirm the robustness and reliability of the developed screening method.

Surprisingly, however, the inventors were able to find a large number of other overexpressed membrane receptors on the infected cells, which are so far not described. The highest increase in cell surface expression was for CD134 (OX40), which is a T cell co-stimulatory molecule and cytokine receptor; see FIG. 2A.

The values indicate the X-fold increase in receptor expression on infected versus non-infected T lymphocytes (n=5, p value for all receptor molecules shown <0.01). Receptors for which an increase in the expression of CD4+ T lymphocytes in HIV infection has already been described are marked in black. For all other white marked receptors the overexpression in HIV infected CD4+ T lymphocytes was unknown and therefore surprising.

Figures 2A, 2B:
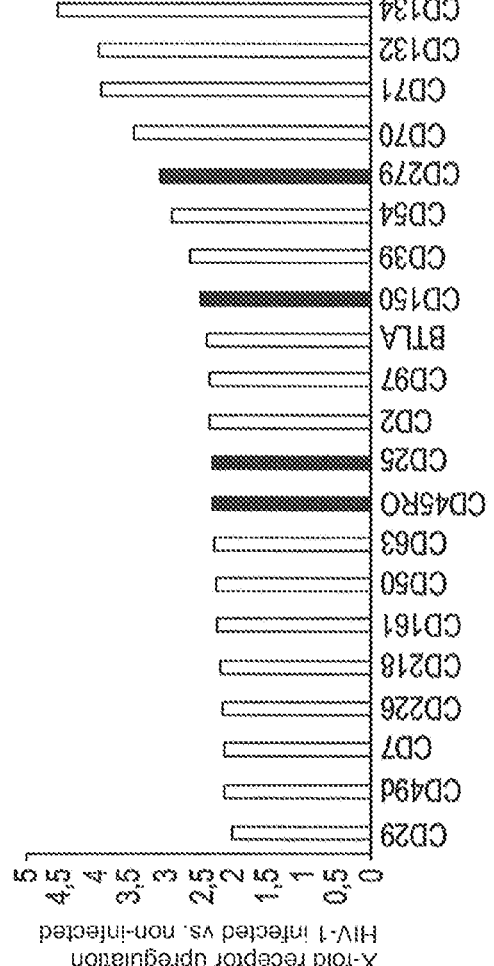
FIG. 2A shows the increase in expression of various membrane receptors on HIV-1 infected versus non-infected primary human CD4$^+$ T lymphocytes.
FIG. 2B shows the increased expression of CD134 on CD4$^+$ T lymphocytes isolated from HIV patients.

CD4+ T lymphocytes were isolated from the blood of HIV-1 infected individuals. The surface of the cells was analyzed for the expression of CD134 and the interior of the cell for p24 of HIV-1. The measurement was carried out by flow cytometry. The result is shown in FIG. 2B.

The graph shows the mean fluorescence intensity (MFI) of CD134 in p24– (not infected) versus p24+ (infected) T cells from ten patients. A statistical calculation was done with the paired student T test. It was thus confirmed that the CD134 expression also strongly increases on infected CD4+ T lymphocytes from the blood of HIV-1 patients.

Thus, based on the CD134 expression, an HIV-1 infected CD4+ T lymphocyte cell can be specifically distinguished from a non-infected cell. CD134 is therefore an ideal target for an anti-HIV-1 immunotherapy.

3. Cytotoxic Agent for the Treatment of an HIV Infection

At present, some antibodies against human CD134 are already available in the state of the art. An example of this is the antibody developed by the company MedImmune with the designation MEDI6469 or 9B12, respectively. This agonistic antibody is currently only used for the treatment of solid tumors. It has already been tested for safety and anti-tumor activity in humans (Curti et al., 2013, loc. cit.). The 9B12 antibody is currently being tested in a clinical trial to determine its suitability for tumor therapy. According to the inventors' findings, this antibody is also potentially suitable for eliminating virus-infected CD4+ T lymphocytes and thus removing the pathogenic viruses from the infected host.

The detection of the cytotoxic property is as follows:

PBMCs are isolated from the blood of healthy donors. The isolated cells are infected with HIV-1 which expresses GFP or CFP. This allows the identification of the infected cell population due to the expression of the chromophore. Various amounts of the anti CD134 antibody, for example MEDI6469 (9B12), are added. An anti-mouse PE is used as the secondary antibody to detect by flow cytometry cells that bind the antibody. This experiment allows to evaluate that the antibody specifically binds to HIV-1 infected cells due to the cellular CD134 expression and not to non-infected cells. It also allows to determine whether different doses have an influence on the level of specific or non-specific binding to HIV-1-infected and non-infected cells.

Next, for a period of 12 days, the viral replication and the amount of infected cells in the HIV-1 infected PBMC-population are observed. Different amounts of the anti-CD134 antibody are added to the infected cultures. At 2 days intervals, the absolute number of infected CD4+ T cells, non-infected CD4+ T cells, the absolute levels of CD3+ cells and of CD8+ T cells which represent cytotoxic T lymphocytes are quantified. The T cell activation and proliferation is analyzed by staining on CD69 and Ki67. The levels of monocytes are measured by the expression of the CD14 receptor.

In addition, the virus production is determined on a reporter cell line by quantifying the release of p24 into the supernatant and the amount of infectious, released virions. Controls include non-infected PBMC cultures with or without treatment with an anti-CD134 antibody and HIV-1 infected PBMC without any treatment. At least three different donors will be analyzed. These experiments allow the conclusion that the CD134 ligation on ex vivo infected primary cells has the potential to eliminate infected cells or suppress viral replication and that non-infected cells are not affected or eliminated by the treatment.

The efficiency of an anti-CD134 treatment can be verified in an established humanized mouse model for the HIV-1 infection. Such a mouse model is provided by the company "Transcure". These mice are infected with HIV-1 and left untreated (n=5) or three different doses of the anti-CD134 antibody were administered (n=5, each dose) to ligate CD134 and specifically eliminate HIV-1 infected cells which express high levels of CD134. The viral load, CD4+ T lymphocyte counts and the percentage of infected cells are observed. Overall, these experiments show that the ligation of CD134 by an antibody directed against this, such as MEDI6469 (9612), has the potential to eliminate HIV-1 infected cells from an organism and thus represents a new anti-HIV-1 immunotherapy.

What is claimed is:

1. A method for the treatment of HIV infection, comprising the administration to a living being in need in a therapeutically effective amount of a cytotoxic agent, and wherein said cytotoxic agent comprises an agonistic antibody, or a fragment thereof, that selective binds to CD134, and said cytotoxic agent is used alone.

2. The method of claim 1, wherein the cytotoxic agent comprises an agonistic antibody that selective binds to the CD134.

3. The method of claim 1, wherein the cytotoxic agent comprises a fragment of an agonistic antibody that selective binds to the CD134.

4. The method of claim 1, wherein the agonistic antibody is selected from the group consisting of: MEDI6469 (9B12), MEDI6383, MEDI0562, and Hu106-222/Hu119-122 (UTMDACC).

5. The method of claim 1, wherein said cytotoxic agent comprises a cytostatic agent.

6. The method of claim 5, wherein the cytostatic agent is selected from the group consisting of: alkylating agents, platinum analogues, intercalants, antibiotics, mitosis inhibitors, and taxanes.

7. The method of claim 1, wherein said cytotoxic agent comprises a virostatic agent.

8. The method of claim 1, wherein the cytotoxic agent consists of an agonistic antibody, or a fragment thereof, that selective binds to the CD134.

* * * * *